(12) United States Patent
Lin et al.

(10) Patent No.: US 9,144,633 B2
(45) Date of Patent: *Sep. 29, 2015

(54) IMPLANTABLE DEVICES COATED WITH INSULIN-MIMETIC VANADIUM COMPOUNDS AND METHODS THEREOF

(75) Inventors: Sheldon S. Lin, Chatham, NJ (US);
David N. Paglia, New Britain, CT (US);
James Patrick O'Connor, Fanwood, NJ (US); Eric Breitbart, South Orange, NJ (US); Joseph Benevenia, Montclair, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 20 days.

This patent is subject to a terminal disclaimer.

(21) Appl. No.: 13/992,927

(22) PCT Filed: Dec. 9, 2011

(86) PCT No.: PCT/US2011/064240
§ 371 (c)(1),
(2), (4) Date: Oct. 18, 2013

(87) PCT Pub. No.: WO2012/079024
PCT Pub. Date: Jun. 14, 2012

(65) Prior Publication Data
US 2014/0044768 A1    Feb. 13, 2014

Related U.S. Application Data

(60) Provisional application No. 61/421,921, filed on Dec. 10, 2010, provisional application No. 61/428,342, filed on Dec. 30, 2010.

(51) Int. Cl.
*A61F 2/28* (2006.01)
*A61L 31/08* (2006.01)
(Continued)

(52) U.S. Cl.
CPC .............. *A61L 31/08* (2013.01); *A61K 9/0024* (2013.01); *A61K 9/0092* (2013.01); *A61K 31/28* (2013.01);
(Continued)

(58) Field of Classification Search
CPC ........................... A61K 9/0024; A61K 9/0092
See application file for complete search history.

(56) References Cited

U.S. PATENT DOCUMENTS

| | | | |
|---|---|---|---|
| 5,019,383 A | 5/1991 | Hopp | |
| 5,061,286 A | 10/1991 | Lyle | |

(Continued)

FOREIGN PATENT DOCUMENTS

| | | |
|---|---|---|
| DE | 10238161 A1 | 2/2004 |
| JP | 03-120257 | 5/1991 |

(Continued)

OTHER PUBLICATIONS

Barrio et al., Vanadium and bone development: putative signaling pathways, Can. J. Physiol. Pharmacol., vol. 84, No. 7, p. 677-686. (Jul. 2006).

(Continued)

*Primary Examiner* — Carlos Azpuru
(74) *Attorney, Agent, or Firm* — Fox Rothschild LLP

(57) ABSTRACT

The present invention discloses vanadium-based insulin-mimetic agent composite coatings, application of these coatings onto implantable devices, and use of the implantable devices for accelerating osseous healing. The invention also encompasses methods of manufacturing implantable devices coated with vanadium-based insulin-mimetic agent composite coatings and the implantable devices so manufactured. The implantable devices have wide applications, including but not limited to treating bone fracture, bone trauma, arthrodesis, and other bone deficit conditions, as well as bone injuries incurred in military and sports activities.

30 Claims, 7 Drawing Sheets

(51) Int. Cl.
  *A61K 9/00* (2006.01)
  *A61K 31/28* (2006.01)
  *A61L 27/54* (2006.01)
  *A61L 31/16* (2006.01)

(52) U.S. Cl.
  CPC ............... *A61L 27/54* (2013.01); *A61L 31/16* (2013.01); *A61L 2300/40* (2013.01); *A61L 2420/04* (2013.01); *A61L 2430/02* (2013.01)

(56) References Cited

U.S. PATENT DOCUMENTS

| | | | |
|---|---|---|---|
| 5,716,415 | A | 2/1998 | Steffee |
| 5,871,779 | A | 2/1999 | Cruz |
| 7,763,582 | B2 | 7/2010 | Lin et al. |
| 8,936,804 | B2 * | 1/2015 | Lin et al. ................ 424/422 |
| 2001/0014662 | A1 | 8/2001 | Rueger et al. |
| 2003/0211170 | A1 | 11/2003 | Gho |
| 2004/0014727 | A1 | 1/2004 | Garrett |
| 2004/0019132 | A1 | 1/2004 | Long et al. |
| 2004/0121025 | A1 | 6/2004 | McKee |
| 2004/0230309 | A1 | 11/2004 | DiMauro et al. |
| 2004/0242953 | A1 * | 12/2004 | Good ............................. 600/7 |
| 2006/0051397 | A1 | 3/2006 | Maier et al. |
| 2006/0093646 | A1 | 5/2006 | Cima et al. |
| 2006/0183729 | A1 | 8/2006 | Uckun |
| 2007/0027543 | A1 | 2/2007 | Gimble et al. |
| 2007/0073385 | A1 * | 3/2007 | Schaeffer et al. ............ 623/1.16 |
| 2007/0181433 | A1 | 8/2007 | Birdsall et al. |
| 2008/0248636 | A1 | 10/2008 | Olander et al. |
| 2009/0104095 | A1 | 4/2009 | Morgan et al. |
| 2009/0214468 | A1 | 8/2009 | Lin et al. |
| 2010/0168854 | A1 * | 7/2010 | Luers et al. ................. 623/11.11 |
| 2010/0211158 | A1 | 8/2010 | Haverty et al. |
| 2010/0226943 | A1 | 9/2010 | Brennan et al. |
| 2011/0004307 | A1 | 1/2011 | Ahn et al. |

FOREIGN PATENT DOCUMENTS

| | | |
|---|---|---|
| JP | 05-140200 | 6/1993 |
| JP | 08-034744 | 2/1996 |
| WO | 96/36333 A1 | 11/1996 |
| WO | 00/24730 A1 | 5/2000 |
| WO | 2009/111300 | 9/2009 |
| WO | 2011/088318 | 7/2011 |
| WO | 2012/079024 A2 | 6/2012 |
| WO | 2013082295 A1 | 6/2013 |

OTHER PUBLICATIONS

Mehdi et al., "Organo-vanadium compounds are potent activators of the protein kinase B signaling pathway and protein tyrosine phosphorylation: Mechanism of insulinomimesis," Arch. Biochem. Biophys., vol. 440, No. 2, p. 158-164. (Aug. 15, 2005).
Millard D. J. Wound Care 4(8):343, 1995.
Kagel Em, et al. Current Opinion in Orthopaedics 6(5):7-13, 1995.
Wildemann B, et al. Bone (34):862-868, 2004.
Cornish, J. et al., Insulin Increases Histomorphometric Indices of Bone Formation in Vivo, Calcif Tissue Intl, 1996, 59:492-495.
Gandhi, A. et al., The Effects of Local Insulin Delivery on Diabetic Fracture Healing, Bone, 2005, pp. 482-490.
Stuck, Walter G., The Effect of Insulin on the Healing of Experimental Fractures in the Rabbit, J. Bone Joint Surg Am., 1932, 14:109-115.
Barrio et al. "Vanadium and bone development: putative signaling pathways", Journal of the All-India Ophthalmological Society 84(7): 677-686. (2006).
Barrio et al. "Potential use of vanadium compounds in therapeutics", Current Medicinal Chemistry 17(31): 3632-3642. (2010).
Arai Michitsugu: "Effects of vanadyl sulfate on osteopenia in streptozotocin-induced diabetic (STZD) rats: Comparison with those of insulin", Folia Pharmacologica Japonica 100(5): 401-414. (1992).
Facchini et al. "The effects of vanadium treatment on bone in diabetic and non-diabetic rats", Bone 38(3): 368-377. (2006).
Cortizo et al. "Osteogenic activity of vanadyl(IV)-ascorbate complex: Evaluation of its mechanism of action", International Journal of Biochemistry and Cell Biology 38(7): 1171-1180. (2006).
Paglia et al. "The effects of local vanadium treatment on angiogenesis and chondrogenesis during fracture healing", Journal of Orthopaedic Research 30(12): 1971-1978. (2012).
Hayao, Ide et al., "Vanadium Promotes Osteogenesis," Health Chemistry, Department of Medicine, Toho University, Omori Medical Center, Toho University [date unknown, office action for Japanese App. 212-549109 on Dec. 25, 2014](Abstract).
Makinen, Marvin et al., "Metabolism and Bioenergetics: Structural Origins of the Insulin-mimetic Activity of Bis(acetylacetonato)oxoyanadium(IV)" J. Biol. Chem., 2002, vol. 277, pp. 12215-12220.
Zhang, Shuang-Qing et al., "Effects on the Bones of Vanadyl Acetylacetonate by Oral Administration: A Comparison Study in Diabetic Rats," J. Bone Miner Metab, (2007), vol. 25, Issue 5, pp. 293-301.
Hamrin et al., "Local effect of vanadate on interstitial glucose and lactate concentrations in human skeletal muscle," Life Sciences (2005), vol. 76, pp. 2329-2338.
Ide et al., "Vanadium promotes osteogenesis" Convention Program Summary of The Japanese Society for Bone and Mineral Research, (2004), vol. 22, p. 171 (Abstract only).
Kishimoto, "Why are not increase of bone density and effect of fracture prevention consistent?" Journal of Osteoporotic Medicine (2005), vol. 4, No. 3, pp. 44-48 (Abstract only).

* cited by examiner

IMPLANTABLE DEVICES COATED WITH INSULIN-MIMETIC VANADIUM COMPOUNDS AND METHODS THEREOF

CROSS-REFERENCE TO RELATED APPLICATIONS

This Application is the U.S. National Phase of International Patent Application No. PCT/US11/64240, filed on Dec. 9, 2011, which claims priority under 35 U.S.C. §119(e) to U.S. Provisional Patent Application Ser. No. 61/421,921, filed on Dec. 10, 2010, Ser. No. 61/428,342, filed on Dec. 30, 2010, and Ser. No. 61/454,061, filed on Mar. 18, 2011. The foregoing applications are hereby incorporated by reference in their entireties.

FIELD OF THE INVENTION

The present invention relates to compositions comprising vanadium compounds as insulin-mimetic agents, application of such insulin-mimetic agent composite surface coatings upon implantable devices, the implantable devices coated with such insulin-mimetic agent composite surface coatings, and methods of using these implantable devices for accelerating bone fracture or osseous healing.

BACKGROUND OF THE INVENTION

Diabetic osteopathy, one of the complications of long-standing, poorly controlled diabetes, leads to diminished bone formation, retardation of bone healing, and osteoporosis. Bone mineral density (BMD) and biomechanical integrity are referential predictors of fracture, and patients with type 1 diabetes incur a higher incidence of fractures compared to healthy individuals. Therefore, BMD and histomorphometry were used to evaluate the potential of drugs to prevent the osteopenia associated with type diabetes (Bain S, et al., *Bone*, 1997; 21(2):147-153; Suzuki K, et al., *Bone*, 2003; 33(1): 108-114). The structural integrity of the femur or tibia was also examined in order to evaluate the biomechanical consequences of diabetes (Reddy G K, et al., *Diabetes Res. Clin. Pract.*, 2001; 54(1):1-8).

In recent years, the potential use of vanadium as an alternative or adjunct treatment for glycemic control of diabetes has been examined (Poucheret P, et al., *Mol. Cell. Biochem.*, 1998; 188(1-2):73-80). For example, vanadyl acetylacetonate (also called bis(acetylacetonate)oxovanadium(IV), $VO(acac)_2$, or VAC) has demonstrated insulin-mimetic effects in studies of type 1 and type 2 diabetic animals (e.g. Crans D C, *J. Inorg. Biochem.*, 2000; 80(1-2):123-131) and humans (e.g., Goldfine A B, et al., *Mol. Cell. Biochem.*, 1995; 153(1-2):217-231) and prevented some of the associated complications of diabetes in animal studies (e.g., Bhanot S, et al., *Mol. Cell. Biochem.*, 1995; 153(1-2):205-209). Additional pharmacological activities of VAC studied include the inhibition of gluconeogenesis (Kiersztan A, *Biochem. Pharmacol.*, 2002; 63(7):1371-1382), a decrease in glutamate dehydrogenase activity (Kiersztan A, et al., *Pharmacol. Toxicol.* 1998; 82(4):167-172), and antilipolysis (Li J, et al., *Endocrinology*, 1997; 138(6):2274-2279).

Several studies have demonstrated VAC improved the ultimate strength, Tb,Th, MAR, and plasma osteocalcin in diabetic rats; however, VAC did not affect any bone parameters in normal rats in this non-injury and non fracture model of bone homeostasis (Facchini D M, et al., *Bone*, 2006; 38(3):368-377; Zhang S Q, et al., *J. Bone Miner. Metab.*, 2007; 25(5): 293-301). The results from an in vitro model using osteoblast-like cells showed that vanadium exerted biphasic effects: a low concentration of vanadium stimulated osteoblast proliferation and differentiation, but a high concentration inhibited these effects (Bain S, et al., *Bone*, 1997; 21(2):147-153; Cortizo A M, et al., *Toxicology*, 2000; 147(2):89-99; Cortizo A M, et al., *Eur. J. Pharmacol.*, 2000; 400(2-3):279-285; Cortizo A M and Etcheverry S B, *Mol. Cell. Biochem.*, 1995; 145(2): 97-102; Suzuki K, et al., *Bone*, 2003; 33(1):108-114). In vivo studies indicate that vanadium therapy can improve bone quality in diabetic animal models (Facchini D M, et al., *Bone*, 2006; 38(3):368-377; Zhang S Q, et al., *J. Bone Miner. Metab.* 2007; 25(5):293-301). However, in vivo evaluation data on bone fracture healing in the presence of vanadium are still unavailable, and no evaluation of vanadium composite as a surface coating on orthopedic devices for bone fracture healing or other bone regenerative processes has been performed.

SUMMARY OF THE INVENTION

The present invention provides insulin-mimetic vanadium composites as surface coatings on orthopedic devices and methods of using such coated devices for accelerating osseous healing or other bone regenerative processes. The methods can accelerate bone regeneration by stimulating insulin signaling at a fracture site.

In one aspect the present invention provides an implantable device coated by a composite surface coating comprising an insulin-mimetic agent. The insulin-mimetic agent is preferably a vanadium compound, more preferably an organovanadium compound.

In another aspect the present invention provides an insulin-mimetic agent composite surface coating for implantable devices, the coating preferably comprising a vanadium compound and more preferably comprising an organovanadium compound.

In another aspect the present invention provides use of an insulin-mimetic agent composite surface coating for manufacture of implantable devices, the insulin-mimetic agent comprising a vanadium compound, preferably an organovanadium compound.

In another aspect the present invention provides a method of promoting bone healing in a patient in need thereof, comprising treating the patient with an implantable device coated by a composite surface coating comprising an insulin-mimetic agent. The insulin-mimetic agent is preferably a vanadium compound, more preferably an organovanadium compound.

In another aspect the present invention provides a method of making an implantable device, the method comprising coating an implant device with an insulin-mimetic agent composite. The insulin-mimetic agent is preferably an organovanadium compound.

This invention, based on a novel concept, provides a significant paradigm shift from the present Orthopedic implant technology by providing a unique Vanadium composite surface coating upon Orthopedic devices. The methods of the present invention are applicable to devices including, but not limited to, plates, rods, screws, implants, arthroplasty implants or orthopedic devices utilized to stabilize fractures, osseous defects or tendon osseous junction in conjunction with the use of allograft/autograft or orthopedic biocomposite.

This invention is able not only to improve the material properties of the implant (by improving the surface hardness) but also to accelerate bone regeneration by the Vanadium composite surface coating of orthopedic device.

The coated "device" of the present invention can take any suitable forms, including but not limited to plates, rods, screws, implants, arthroplasty implants or orthopedic devices utilized to stabilize fractures, osseous defects, to treat delayed union/non union, for allograft/autograft incorporation, or tendon/ligament osseous junction healing as well as allograft/autograft or orthopedic biocomposite incorporation.

Surface modification of the orthopedic implants provides significant advantages including, but not limited to, ease of use, improved material properties, simple sterilization protocols, lack of storage (i.e., refrigeration) needs, and ability to use existing orthopedic devices made out of titanium, zirconium, cobalt-chrome, stainless steel, and other specialty metals or their alloys to achieve accelerated bone regeneration by coating the devices with a unique Vanadium composite.

These and other aspects of the present invention will be better appreciated by reference to the following drawings and detailed description.

DETAILED DESCRIPTION OF THE INVENTION

Figure 1:
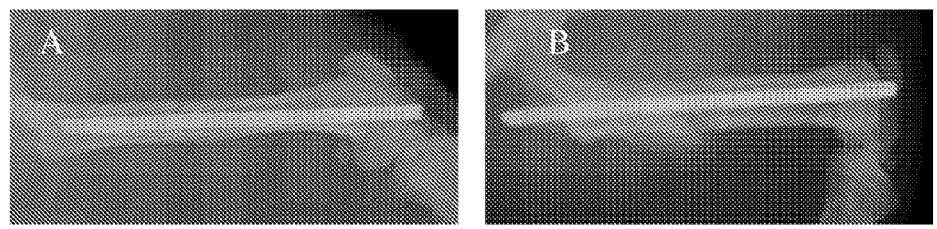
FIG. 1 represents post-operative X-ray photographs taken immediately post-operation. (A) Einhorn model, (B) model used in this invention. (Note in (B): the Kirschner wire is going through the trochanter, which helps to stabilize the fracture site and prevent migration of the Kirschner wire).

The present invention relates to implantable devices coated with insulin-mimetic agents, in particular vanadium compounds or compositions thereof, and use of these implantable devices for treatment of bone fractures.

Although insulin or insulin-like growth factor treatment can be used to stimulate fracture healing in both diabetic and healthy, non-diabetic animal models (Gandhi A, et al., *Bone*, 2005; 37(4):482-490; Gandhi A, et al., *Bone*, 2006; 38(4): 540-546), development of a therapy using vanadium-coated implantable devices would obviate the need for developing specialized methods to deliver growth factors and thereby reduce costs associated with therapy, eliminate specialized storage, and enhance ease of use.

Thus, in one aspect the present invention provides an implantable device coated by a composite surface coating comprising an insulin-mimetic agent.

In one embodiment of this aspect, the insulin-mimetic agent composite coating comprises a vanadium compound. Vanadium compounds suitable for the present invention can be those of vanadium (III), (IV), or (V), especially (IV) or (V), for example, in the form of vanadate ($V^{+5}$), e.g., $VO_4^{3-}$, or in the form of vanadyl ($V^{+4}$) compounds, e.g., vanadyl sulfate ($VOSO_4$). Although use of the vanadium compounds described previously for the treatment of diabetes are especially preferred, other physiologically tolerable vanadium salts or complexes, either inorganic or organic, can be used.

In a preferred embodiment the insulin-mimetic agent is an organovanadium compound. The organovanadium compounds have a structure of formula $VOL_2$ or $VO(OR)L_2$, wherein L is a bidentate monoprotic ligand, and R is an organic group. The bidentate monoprotic ligand can be, for example, a hydroxamate, thiohydroxamate, 2,4-dione, α-hydroxypyrone, α-hydroxypyridinone, or other bidentate monoprotic groups. R is selected from $C_1$-$C_6$ alkyl, phenyl, benzyl or $C_2$-$C_6$ alkenyl group, each optionally substituted by one to three substituents independently selected from hydroxyl, $C_1$-$C_4$ and halogen.

In a more preferred embodiment the insulin-mimetic agent is selected from the group consisting of vanadyl acetylacetonate (VAC), vanadyl sulfate (VS), vanadyl 3-ethylacetylacetonate (VET), and bis(maltolato)oxovanadium (BMOV).

In another embodiment the implantable device is selected from the group consisting of plates, rods, screws, implants, arthroplasty implants, and orthopedic devices.

In another preferred embodiment the implantable device is a bone implant.

In another aspect the present invention provides an insulin-mimetic agent composite surface coating for implantable devices, the coating comprising a vanadium compound.

In one embodiment the insulin-mimetic agent comprises an organovanadium compound.

In a preferred embodiment the insulin-mimetic agent is selected from the group consisting of vanadyl acetylacetonate (VAC), vanadyl sulfate (Vs), vanadyl 3-ethylacetylacetonate (VET), and bis(maltolato)oxovanadium (BMOV).

in another aspect the present invention provides use of an insulin-mimetic agent composite surface coating for manufacture of an implantable device, the insulin-mimetic agent comprising a vanadium compound, preferably an organovanadium compound.

In another aspect the present invention provides a method of promoting bone healing in a patient in need thereof, comprising treating the patient with an implantable device coated by a composite surface coating comprising an insulin-mimetic agent. The insulin-mimetic agent is preferably an organovanadium compound according to any embodiments described herein.

In one embodiment of this aspect, the insulin-mimetic agent comprises a vanadium compound.

In a preferred embodiment the insulin-mimetic agent is an organovanadium compound.

In a more preferred embodiment the insulin-mimetic agent is an organovanadium compound selected from the group consisting of vanadyl acetylacetonate (VAC), vanadyl sulfate (VS), vanadyl 3-ethylacetylacetonate (VET), and bis(maltolato)oxovanadium (BMOV). In a most preferred embodiment the insulin-mimetic agent is VAC.

In another embodiment the implantable device is selected from the group consisting of plates, rods, screws, implants, arthroplasty implants, and orthopedic devices.

In a preferred embodiment the implantable device is a bone implant.

The present invention is suitable for bone healing in any patients afflicted with a bone condition selected from the group consisting of bone fracture, bone trauma, arthrodesis, and a bone deficit condition associated with post-traumatic bone surgery, post-prosthetic joint surgery, post-plastic bone surgery, post-dental surgery, bone chemotherapy treatment, congenital bone loss, post traumatic bone loss, post surgical bone loss, post infectious bone loss, allograft incorporation or bone radiotherapy treatment.

In another embodiment of this aspect, the treatment method is used in conjunction with administration of a cytotoxic agent, cytokine or growth inhibitory agent.

In another embodiment the method is used in conjunction with administration of a bioactive bone agent.

In another embodiment the method is used for treatment of fractures, osseous defects, delayed union or non-union, allograft/autograft incorporation or tendon/ligament osseous junction.

In another embodiment the method is used in conjunction with an allograft/autograft or orthopedic biocomposite.

In another embodiment the patient is a mammalian animal.

In a preferred embodiment the patient is a human.

In another preferred embodiment the patient is a non-diabetic human patient.

In another aspect the present invention provides a method of making an implantable device, the method comprising coating an implant device with an insulin-mimetic agent composite.

In one embodiment the insulin-mimetic agent is an organovanadium compound.

In a preferred embodiment the insulin-mimetic agent is selected from the group consisting of vanadyl acetylacetonate (VAC), vanadyl sulfate (VS), vanadyl 3-ethylacetylacetonate (VET), and bis(maltolato)oxovanadium (BMOV).

In another embodiment the implantable device is selected from the group consisting of plates, rods, screws, implants, arthroplasty implants, and orthopedic devices.

In another preferred embodiment the implantable device is a bone implant.

In any of the aspects of the present invention described above, other suitable organovanadium compounds include, but are not limited to, those disclosed in U.S. Pat. Nos. 5,300,496; 5,527,790; 5,620,967; 5,688,784; 5,866,563; 5,888,993 and 6,268,357 to J. H. McNeill and C. Orvig et al., all of which are hereby incorporated by reference. The complexes, most of which are vanadyl hydroxamates or thiohydroxamates, include, but are not limited to bis(kojato)oxovanadium (IV) (vanadyl Kojate) (Kojic acid=2-hydroxymethyl-5-hydroxy-γ-pyrone); bis(3-oxy-1,2-dimethyl-4-pyridinonato)-oxovanadium(IV) (VO(dpp)$_2$); bis(2-hydroxymethyl-5-oxy-1-methyl-4-pyridinonato)-oxovanadium(IV) (VO(hmp)$_2$); bis[2-(2'-oxyphenyl)-2-oxazolinato]-oxovanadium(IV) (VO (tz)$_2$); bis[2-(2'-oxyphenyl)-2-thiazolinato]-oxovanadium (IV) (VO(tz)$_2$), bis(benzohydroxamato)-oxovanadium(IV) (VO(bz)$_2$); bis(benzohydroxamato)-methoxooxovanadium (V) (VO(OCH$_3$)(bz)$_2$); bis(benzohydroxamato)ethoxooxovanadium(V) (VO(OC$_2$H$_5$)(bz)$_2$); bis(salicylaldehyde)-oxovanadium(IV) (VO(Sal)$_2$); ammonium bis(maltolato)-dioxovanadate; bis(ethylmaltolato)oxovanadium(IV) (VO (ema)$_2$) and EthylBMOV).

Suitable organovanadium complexes also include oxovanadium(IV)-biguanide complexes and derivatives as described in U.S. Pat. No. 6,287,586 to Orvig and McNeill, which is hereby incorporated by reference, for example, oxovanadium(IV) biguanide (VO(big)$_2$), oxovanadium(IV) metformin (VO(met)$_2$), and oxovanadium(IV) phenformin (VO (phen)$_2$)).

Suitable organovanadium compounds also include vanadyl cysteine complexes disclosed in EP Patent No. 305,264 to Lazaro et al. or in JP-A-2-2/292217 to Komatsu et al., both of which are hereby incorporated by reference. These vanadyl cysteine complexes were described to be used for oral treatment of diabetes.

Optionally, and sometimes preferably, the method of the present invention is used in conjunction with local administration of a same or different vanadium-based insulin-mimetic agent as disclosed in U.S. Provisional Application No. 61/295,243, filed Jan. 15, 2010, and PCT Application No. PCT/US2011/021296, filed Jan. 14, 2011, both of which are hereby incorporated by reference in their entirety for all purposes.

Although the present invention is not limited by any theory, an insulin-mimetic coating on an implantable device of the present invention would result in a different biodistribution from that of a local solution intramedullary injection method. In addition, the present invention provides benefits including, among others, a) directed local delivery; b) less risk of systemic release into the blood stream or drug system collapse; c) less complications of soft tissue/bony alterations as less effect on the contiguous tissue; and d) lower dosage required to achieve goals of bone healing acceleration.

Current simple and comminuted fracture treatment relies upon restoring the bone's anatomy and stabilizing the fractured bone until the body is able to heal the fracture with newly produced bone. Adjuncts to this basic procedure such as a method to significantly enhance bone regeneration while maintaining appropriate blood flow and preventing infection have the potential to revolutionize this field. Osseous agents such as Vanadium compounds can enhance fracture callus strength by exploiting the healing responsiveness of insulin pathways. A therapy of this non-protein agent coated on implantable devices has a minimal possibility of infection or systemic consequences associated with systemic treatments.

Preliminary data has indicated that local Vanadium treatment is an effective method to treat non-diabetic patients who sustain fractures. Mechanical parameters and microradiography revealed that bone has bridged at 4 weeks post fracture. Spiral fractures that occurred during mechanical testing reaffirm this phenomenon and suggest that local VAC application at the dosages tested without a carrier may heal bone more than twice as rapidly as saline controls. This evidence opens up many future applications to the use of VAC alone, or incorporated with a carrier as an option for fracture healing.

One particular useful application of the present invention is, for example, in the treatment of military injuries involving bone fractures.

In the recent United States conflicts, significant improvements in personal body armor have led to fewer casualties. While this advancement in personal protection has reduced the number of mortalities, the morbidity of war, specifically a dramatically larger portion of battle-related injuries, has occurred in the extremities. Depending upon the level of energy, extremity fracture may range from simple closed fracture to large segmental defects with a significant bone and soft tissue loss evident. Battle-related fractures have very high complication rates (47% in one study) with delayed union and non-union in 31% of all the fractures followed (Pukljak D, *J. Trauma.*, 1997; 43(2):275-282). Many of these fractures occur in the extremities. The kinetic energies of bullet wounds often severe due to the large amount of kinetic energy expends on the bone surface.

Using principles learned from previous wars and the development of Level I trauma centers, orthopedics care relies on the timely principles of restoration of anatomy, appropriate osseous stabilization, and the subsequent restoration of function. Potential adjuncts to this basic concept either through mechanical means (i.e. low intensity pulse ultrasound) or biological means (growth factors such as BMP-2 or the like) can lead to an acceleration of osseous healing with faster return to health and duty.

The high complication rate of severe military injuries with delayed union and non-unions parallels the observations seen in the civilian population who have risk factors for impaired bone healing. Risk factors include smoking, old age, steroid use, certain pharmaceuticals (i.e. anti-cancer drugs) and diabetes mellitus (DM). Clearly, if one is able to solve the impaired osseous healing associated with high-risk populations, one should be able to accelerate fracture healing in the normal, young, healthy soldiers with an insulin mimetic compound. The present invention provides such a solution that would at least partially solve the problem.

Because up to 10% of the 6.2 million fractures sustained annually proceed to delayed union and non-union (Praemer A and Rice D, *Am. Acad. Orhtop. Surg.*, 1992:85-124), development of an ideal osseous adjunct would ameliorate significant military issues and, to a greater extent, clinical challenges throughout the United States.

The application of a unique Vanadium composite surface coating upon orthopedic devices at the fracture site can have even wider scope of applications. For example, the unique Vanadium composite surface coating upon Orthopedic devices can find applications in treating both non-unions and delayed unions, for Orthopedic use in trauma settings, and in sports medicine to treat a variety of fractures including fatigue fractures and acute sports-related fractures, such as acute fractures incurred during athletic activities as a result of overloading bone (boot top tibial fractures in skiing) or from ligament to tendon avulsion (tibial tubercle avulsion during long jumping). High school football injuries alone account for over 38,000 annual fractures (DeCoster T A, et al., *Iowa Orthop. J.*, 1994; 14:81-84). Sports fractures include, but are not limited to, tibial (49%), femoral (7%), and tarsal (25%) fractures, which may differ depending on the individuals and causes of injury. The present work examined a mid-diaphyseal fracture pattern, but it is likely that other fracture patterns would heal in the same fashion.

The coatings of present invention can be formed by any methods known in the relevant art, for example, without limitation, those disclosed in Petrova and Suwattananont, *J. Electr. Mat.*, 2005; 34(5):575-582, and references cited therein. For example, suitable methods include chemical vapor deposition (CVD), physical vapor deposition (PVD), thermochemical treatment, oxidation, and plasma spraying. A suitable coating of the present invention may also contain combinations of multiple, preferably two or three, layers obtained by forming first boron diffusion coating followed by CVD. Thermochemical treatment techniques have been well investigated and used widely in the industry. This is a method by which nonmetals or metals are penetrated by thermodiffusion followed by chemical reaction into the surface. By thermochemical treatment, the surface layer changes its composition, structure, and properties.

Other suitable coating techniques may include, but are not limited to, carburizing, nitriding, carbonitriding, chromizing, and aluminizing. Among these coating techniques, boronizing, being a thermochemical process, is used to produce hard and wear-resistant surfaces. Thermal diffusion treatments of boron compounds used to form iron borides typically require process temperatures of 700-1000° C. in either gaseous, solid, or salt media (Erdemir A and Bindal C, *Surf Coating Technol.*, 1995; 76-77:443-449; Pengxun Y. *Thin Solid Films*, 1992; 214, 44; Hu R, et al., *Surf Coating Technol.*, 1990, 42:282). Boronizing is a process by which active boron atoms diffuse into the surface of substrate metal or alloy in order to produce a layer of borides. This treatment can be applied to ferrous materials, certain nonferrous materials such as titanium, tantalum, niobium, zirconium, molybdenum, nickel-based alloys, and cermets. Borides formed on steel surfaces increase their hardness (to about 2000 HV), wear resistance, and corrosion resistance. Diffusion boronizing forms boride layers on metal and steel with good surface performance. Other developments in boronizing include gas boronizing techniques such as fluidized bed boronizing and plasma boronizing. Physical vapor deposition and CVD, plasma spraying, and ion implantation are alternative non-thermochemical surface coating processes for the deposition of boron or co-deposition of boron and metallic elements onto a suitable metallic on nonmetallic substrate material.

As a person of ordinary skill in the art would understand, different coating techniques may be used to make the vanadium-based coatings and coated devices of the present invention in order to have desired properties suitable for the intended purposes.

One major concern related to the long-term administration of a vanadium compound is a significant vanadium accumulation in bones. The accumulation of vanadium, especially if given in a daily regimen, could potentially be toxic to bones and the marrow within. A pharmacokinetic study by Zhang, et al, (Zhang S Q, et al., *J. Inorg. Biochem.*, 2005; 99(5):1064-1075) showed that while VAC was widely distributed to all tissues, the greatest accumulation was within femur tissue. The average elimination half-life values of VAC in femur tissue was 657.3±77.9 h (27.4±3.2 days), similar to those of the other vanadium compounds. However, unlike other vanadium compounds which caused obvious signs of toxicity, such as diarrhea, VAC appeared to be better tolerated with no signs of toxicity after several days. Nevertheless, because of the limited current work with VAC and other vanadium compounds, the tolerance for longer-term oral administration of VAC and its effects upon bone are still unknown. Therefore, quantification of VAC in several bones and tissues is being examined to determine the half-life of vanadium after a single local dose.

As shown below, the amount of vanadium (V) per application is down at the levels of approximately 280 μg/implantation (Table 1).

TABLE 1

Analysis of surface coated rod for Vanadium content

| Description | SS-rod[a] | B-SS-rod[b] | V-B-SS-rod[c] |
|---|---|---|---|
| Weight of rod (g) | 0.2692 | 0.2713 | 0.2828 |
| Length of rod (mm) | 40 | 40 | 40 |
| *Mean V μg/g | 725.7 | 391.3 | 1037.1 |
| StdDev V μg/g | 12.2 | 28.9 | 2 |
| V % | 0.073 | 0.039 | 0.104 |
| Mean V μg/mm | 4.9 | 2.7 | 7.3 |
| StdDev μg/mm | 0.08 | 0.2 | 0.01 |

[a] Stainless steel rod.
[b] Boronized stainless steel rod.
[c] VAC-Boronized Stainless steel rod.

Use of the vanadium-coated implantable devices of the present invention for treatment of bone fractures is advantageous also because of limited toxic effects of vanadium compounds, such as VAC Studies on the effects of accumulation of vanadium in other organ systems have revealed that VAC treatment does not impair the function or structure of kidney and liver (Zhang S Q, et al., *J. Bone Miner. Metab.,* 2007; 25(5):293-301), which is consistent with study of vanadyl sulfate (Dai S, et al., *Pharmacol. Toxicol.,* 1994; 74(2):101-109; Dai S, et al., *Pharmacol. Toxicol.,* 1994; 75(5):265-273). Nevertheless, examination of vanadium on other organs and systems is being evaluated in conjunction with the present invention to assess any toxicity issues of vanadium.

Vanadium, which exists in +4 (vanadyl) and +5 (vanadate) compounds in the biological body, have demonstrated poor absorption rates within the gastrointestinal (GI) tract and GI side-effects, such as diarrhea and vomiting. Thus, the present invention, through using vanadium composite-coated devices, provides a novel approach to overcome these shortcomings. In addition, organic vanadium compounds, such as vanadyl sulfate (VS), vanadyl 3-ethylacetylacetonate (VET), bis(maltolato)oxovanadium (BMOV), and vanadyl acetylacetonate (VAC) can increase safety, improve absorption, and reduce undesirable side effects associated with therapeutic vanadium. Therefore, the insulin-mimetic organic vanadium compounds used in the present invention can further improve absorption and safety that may be associated with administration of vanadium compounds for healing bone fractures.

EXAMPLES

Materials and Methods

The BB Wistar Rat Model
Animal Source and Origin

Diabetic Resistance (DR) BB Wistar rats used in the study were obtained from a breeding colony at UMDNJ-New Jersey Medical School (NJMS). The rats were housed under controlled environmental conditions and fed ad libitum. All research protocols were approved by the Institutional Animal Care and Use Committee at University of Medicine and Dentistry of New Jersey-New Jersey Medical School.
Diabetic Resistant BB Wistar Rats A total of 13 DR BB Wistar rats were utilized in the study. Due to unstable fixation of mechanical testing, one sample was removed. The remaining 12 animals were used for mechanical testing, distributed amongst the control saline (n=5), Boron coated rods (n=3) and Vanadium-Boron coated rods (n=4) groups.
Closed Femoral Fracture Model Surgery was performed in DR animals between ages 80 and 120 days, using a closed mid-diaphyseal fracture model, on the right femur as described previously (Beam H A, et al., *J. Orthop. Res.,* 2002; 20(6):1210-1216; Gandhi A, et al., *Bone,* 2006; 38(4):540-546).

General anesthesia was administered by intraperitoneal (IP) injection of ketamine (60 mg/kg) and xylazine (8 mg/Kg). The right leg of each rat was shaved and the incision site was cleansed with Betadine and 70% alcohol. An approximately 1 cm medial, parapatellar skin incision was made over the patella. The patella was dislocated laterally and the interchondylar notch of the distal femur was exposed. An entry hole was made with an 18 gauge needle and the femur was reamed with the 18 gauge needle. A Kirschner wire (316LVM stainless steel, 0.04 inch diameter, Small Parts, Inc., Miami Lakes, Fla.) which underwent thermochemical pack boriding was inserted the length of the medullary canal, and drilled through the trochanter of the femur. The Kirschner wire was cut flush with the femoral condyles. After irrigation, the wound was closed with 4-0 Vicryl resorpable suture. A closed mid-shaft fracture was then created unilaterally with the use of a three-point bending fracture machine. X-rays were taken to determine whether the fracture is of acceptable configuration. An appropriate fracture is an approximately mid-diaphyseal, low energy, transverse fracture (FIG. 1). The rats were allowed to ambulate freely immediately post-fracture. This closed fracture model is commonly used to evaluate the efficacy of osseous wound healing devices and drugs.
Experimental Treatments
Orthopedic Device: IM Rod Pack Solid Bonding Technique During boriding of steel and other metallic and alloy surfaces, boron atoms diffuse into the material and form various types of metal borides. In the case of ferrous alloys, most prominent borides are: $Fe_2B$ and FeB. ($Fe_3B$ may also form depending on the process parameters). Some of the boron atoms may dissolve in the structure interstitially without triggering any chemical reaction that can lead to boride formation. Iron borides (i.e., $Fe_2B$ and FeB) are chemically stable and mechanically hard and hence can substantially increase the resistance of base alloys to corrosion, oxidation, adhesive, erosive, or abrasive wear. Process conditions (such as duration of boriding, ambient temperature, type of substrate material and boriding media) may affect the chemistry and thickness of the borided surface layers. Due to the much harder nature of borided layers, boriding has the potential to replace some of the other surface treatment methods like carburizing, nitriding and nitrocarburizing.

Boride layers may achieve hardness values of more than 20 GPa depending on the chemical nature of the base materials. $TiB_2$ that forms on the surface of borided titanium substrates may achieve hardness values as high as 30 GPa; $ReB_2$ that forms on the surface of rhenium and its alloys may achieve hardness values as high as 50 GPa, while the hardness of boride layers forming on steel or iron-based alloys may vary between 14 GPa to 20 GPa. Such high hardness values provided by the boride layers are retained up to 650° C. Since there is no discrete or sharp interface between the boride layer and base material, adhesion strengths of boride layers to base metals are excellent. With the traditional methods mentioned above, boride layer thicknesses of up to 20 micrometer can be achieved after long periods of boriding time at much elevated temperatures. In addition to their excellent resistance to abrasive, erosive, and adhesive wear, the boride layers can also resist oxidation and corrosion even at fairly elevated temperatures and in highly acidic or saline aqueous media.
Vanadium Composite Surface Coating Upon Orthopedic Devices: IM ROD Manufacturing During boriding of steel and other metallic and alloy surfaces, boron atoms diffuse into the material and form various types of metal borides.

Figure 6A:
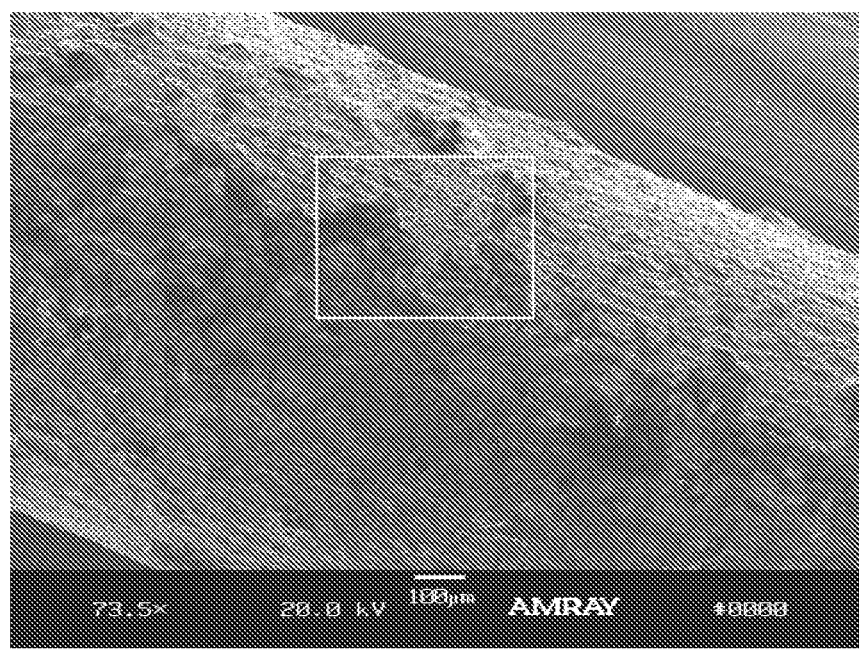
FIG. 6 contains analysis results of a first Ti6Al4V implant sample using scanning electron microscope (SEM) and energy-dispersive X-ray spectroscopy (EDX): (A) SEM image as visualized under SEM at 73.5× (scale 100 µm); and (B) the results of EDX elemental analysis weight and atomic percentages.
Figure 7A:
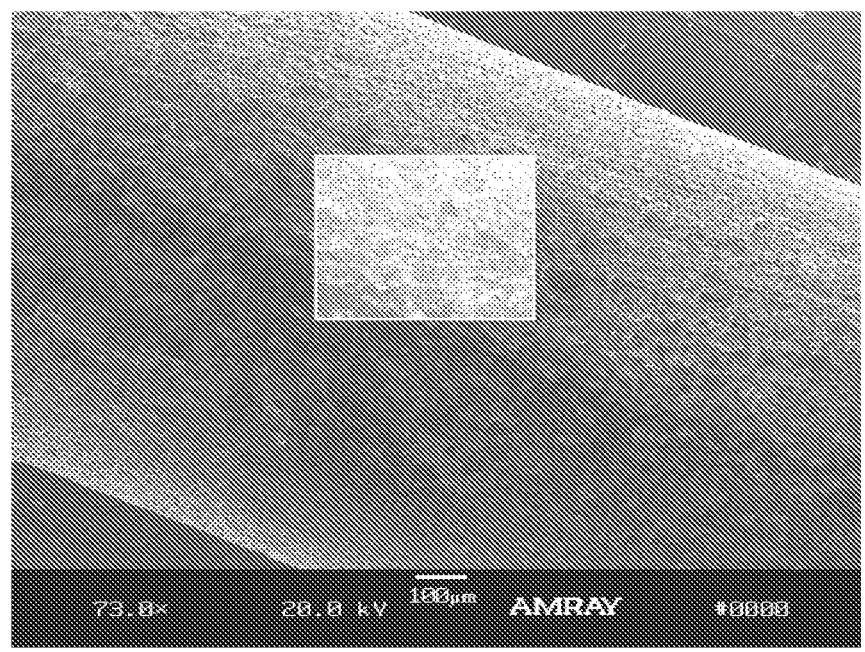
FIG. 7 contains analysis results of a second Ti6Al4V implant sample using scanning electron microscope (SEM) and energy-dispersive X-ray spectroscopy (EDX): (A) SEM image as visualized under SEM at 73.0× (scale 100 µm); and (B) the results of EDX elemental analysis weight and atomic percentages.

Annealed, cleaned, 1.6 mm Kirschner wire (316LVM stainless steel, 0.04 inch diameter, Small Parts, Inc., Miami Lakes, Fla.) was packed in a boriding powder mixture contained within a 5 mm thick, heat resistant steel box. This allows the surfaces to be borided with a layer that is 10-20 micrometer thick. A mixture of boron carbide, vanadium (vanadyl acetylacetonate (VAC), Sigma Aldrich, St. Louis, Mo.) silicon carbide, and a boriding activator were pact borided according to an industry standard protocol (Petrova R. and Suwattananont N., *J. Electr. Mat.,* 2005, 34(5):8). The parts conformed to the container which they were packed, and then covered with a lid, which rests inside the container. This container was then weighted with an iron slug to ensure even trickling of the boriding agent during the manufacturing. The container was then heated to the boriding temperature as described in an electrically heated box with covered heating coils. The coated rods were allowed to cool to room temperature and wiped with 95% ethyl alcohol prior to surgery. In a similar fashion, cleaned 1.6 mm Kirschner wire (Ti6Al4V, 0.04 inch diameter, Small Parts, Inc., Miami Lakes, Fla.) was treated in a similar process to 1000° C. with only VAC powder in order to achieve a Vanadium composite surface coating upon Orthopedic implant. A scanning electron microscope (SEM) was used to image samples by scanning it at 12.7× (scale 1 mm) and 73.0×–73.5×(scale 100 µm) with a high-energy beam of electrons in a raster scan pattern. Electrons interact with the atoms that make up the sample producing signals that contain information about the sample's surface topography, composition, etc. This method was used to observe surface topography to confirm that VAC powder was coated as a film-layer on the surface of implants. FIGS. 6(A) and 7(A) contain SEM images of samples coated with different concentrations of VAC.

Figure 6B:
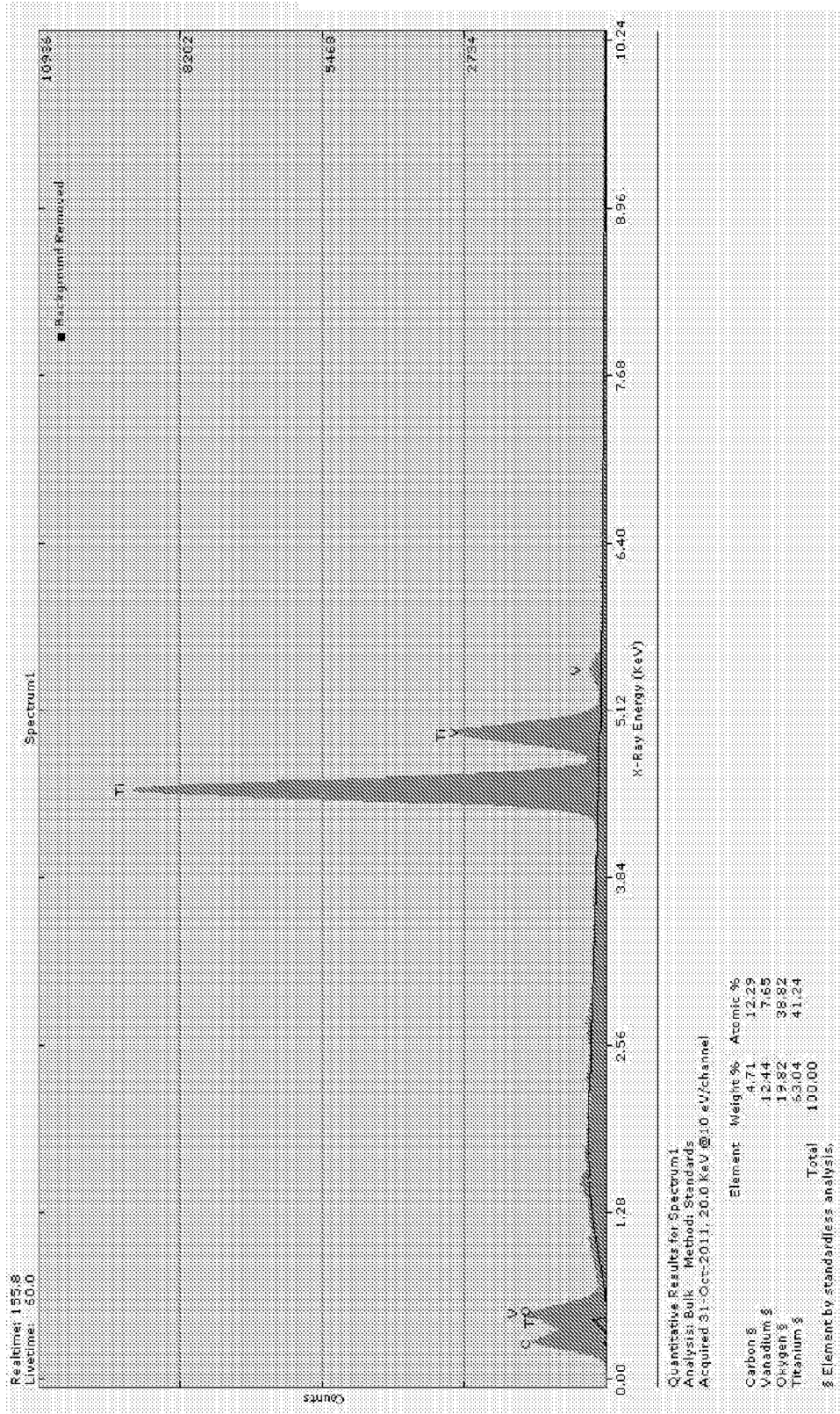
Figure 7B:
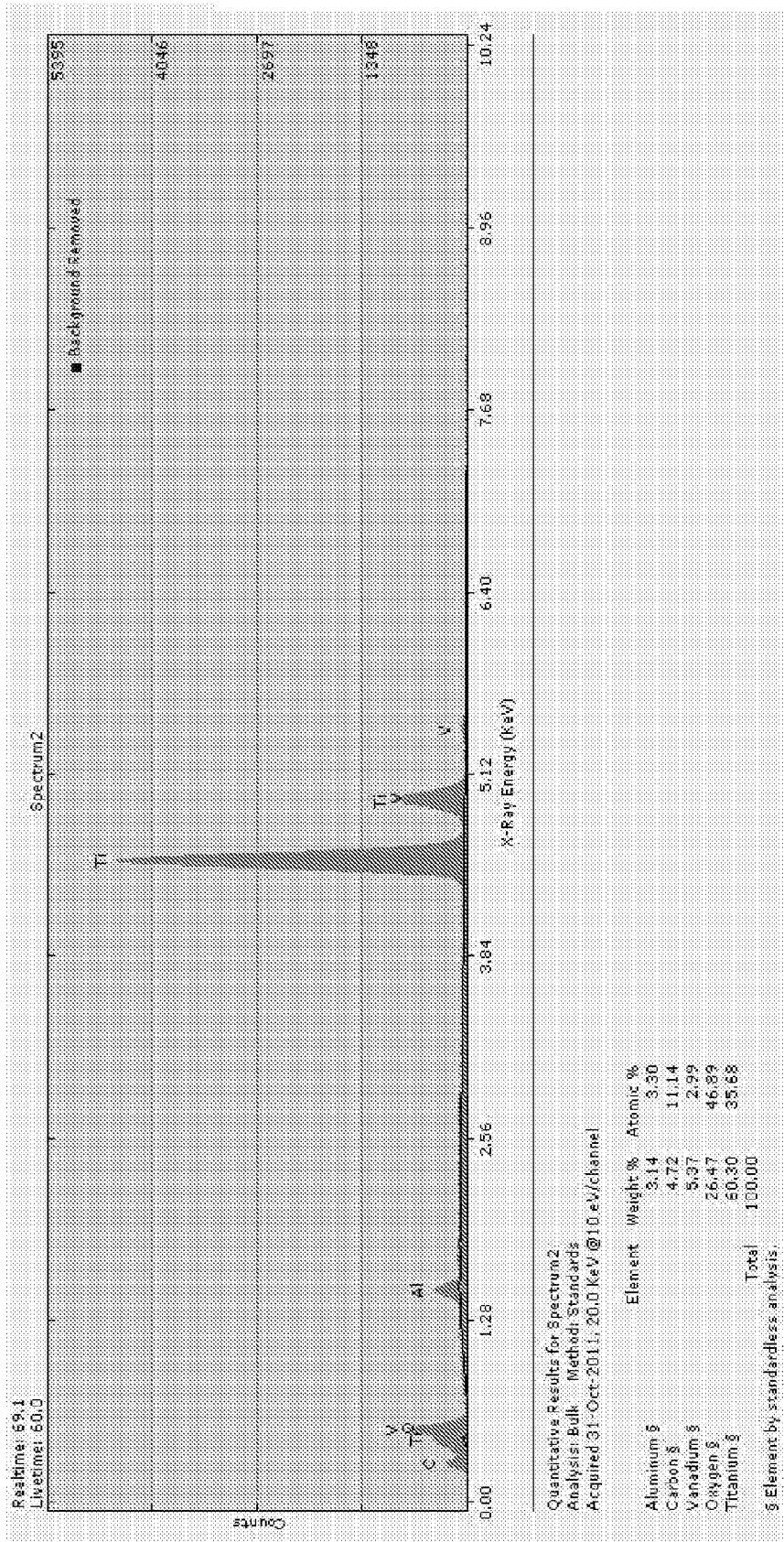

Energy-dispersive X-ray spectroscopy (EDX), an analytical technique used for the elemental analysis/chemical characterization of a sample, was used to analyze vanadium concentrations coated to samples. It relies on the investigation of an interaction of X-ray excitation and the coated rods. EDX characterization capabilities are due mainly to the fundamental principle that each element has a unique atomic structure allowing X-rays that are characteristic of an element's atomic structure to be identified uniquely from one another. X-ray energy was measured in kilo-electron volts. Elemental analysis determined weight and atomic percentages of two independent rod samples (FIGS. 6(B) and 7(B)).

Microradiographic Evaluation

Serial microradiographs were obtained from all animals every two weeks post-surgery. Under the same anesthesia as described previously, the rats were positioned prone so lateral and anteroposterior (AP) views of their femurs could be obtained. Radiographs were taken using a Hewlett-Packard Faxitron (Model 43804—Radiographic Inspection System) and Kodak MinR-2000 mammography film. Exposures were performed for 30 seconds at 55 kVp. Additionally, magnified radiographs were obtained after the femurs were removed from the animals post-sacrifice. Qualitative analysis was performed on all radiographic samples. Two independent observers individually scored radiographs based on endosteal and cortical bridging on both lateral and AP femoral orientations. Averages amongst samples of the same group were computed to determine overall percentages of endosteal and cortical healing at 4 weeks.

All analysis was conducted in a blinded fashion using a five-point radiographic scoring system, 0=partial callus formation, 1=definite callus with bony union on one cortex, 2=definite callus with bony union on two cortices, 3=definite callus with bony union on two cortices, and 4=definite callus with bony union on all four cortices.

Mechanical Testing

Figure 2:
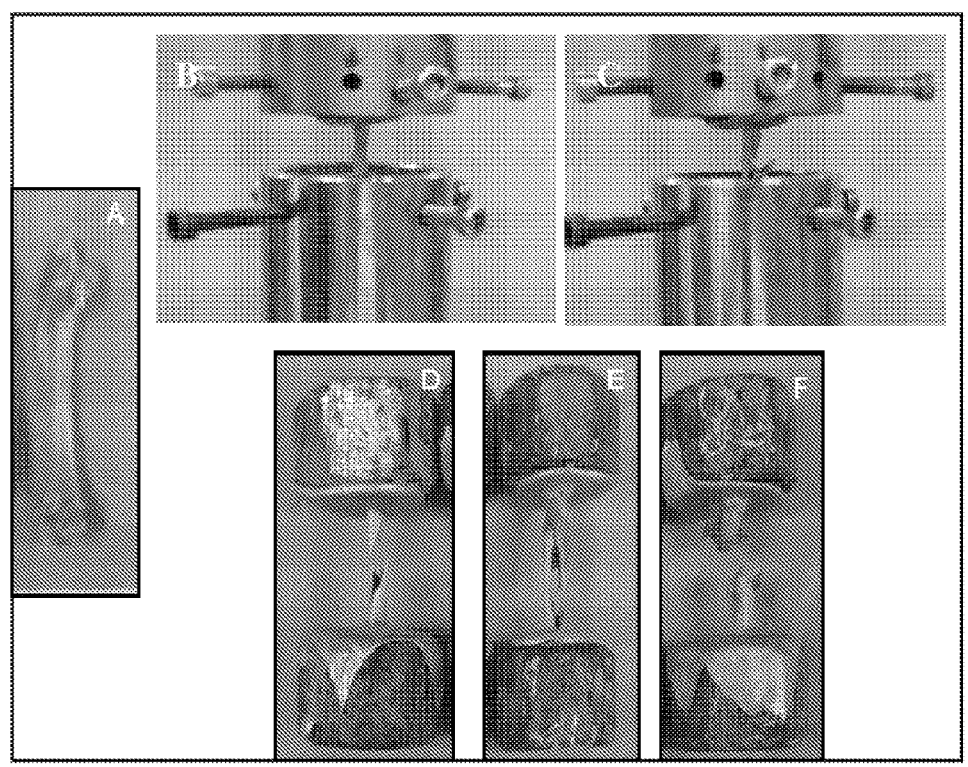
FIG. 2 illustrates a Mechanical Testing Setup: (A) intact femur before embedded in ¾ inch square nut with Field's Metal, (B) intact femur embedded in hex nut and mounted in the mechanical testing apparatus, (C) intact femur mounted in the mechanical testing apparatus after torsional testing, (D) intact femur after torsional testing, (E) fractured femur after torsional testing showing spiral fracture indicative of healing, (F) fractured femur after torsional testing showing non-spiral fracture indicative of non-union.

Fractured and contralateral femora were resected 4 weeks post-fracture. Femora were cleaned of soft tissue and the intramedullary rod was removed. Samples were wrapped in saline (0.9% NaCl) soaked gauze and stored at –20° C. Prior to testing, all femora were removed from the freezer and allowed to thaw to room temperature for three to four hours. The proximal and distal ends of the fractured and contralateral femora were embedded in ¾ inch square nuts with Field's Metal, leaving an approximate gauge length of 12 mm (FIG. 2). After measuring callus and femur dimensions, torsional testing was conducted using a servohydraulics machine (MTS Systems Corp., Eden Prairie, Minn.) with a 20 Nm reaction torque cell (Interface, Scottsdale, Ariz.) and tested to failure at a rate of 2.0 deg/sec. The maximum torque to failure and angle to failure were determined from the force to angular displacement data.

Peak torque to failure ($T_{max}$), torsional rigidity (TR), shear modulus (SM), and maximum torsional shear stress (SS) were calculated through standard equations (Ekeland A, et al., *Acta Orthop. Scand.*, 1981; 52(6):605-613; Engesaeter L B, et al., *Acta Orthop. Scand.*, 1978; 49(6):512-518). $T_{max}$ and TR are considered extrinsic properties while SM and SS are considered intrinsic properties. $T_{max}$ was defined as the point where an increase in angular displacement failed to produce any further increase in torque. TR is a function of the torque to failure, gauge length (distance of the exposed femur between the embedded proximal and distal end) and angular displacement. SS is a function of the torque to failure, maximum radius within the mid-diaphyseal region and the polar moment of inertia. The polar moment of inertia was calculated by modeling the femur as a hollow ellipse. Engesaeter et al. demonstrated that the calculated polar moment of inertia using the hollow ellipse model differed from the measured polar moment of inertia by only two percent (Engesaeter L B, et al., *Acta Orthop. Scand.*, 1978; 49(6):512-518).

In order to compare the biomechanical parameters between different groups, the data was normalized by dividing each fractured femur value by its corresponding intact, contralateral femur value. Normalization was used to minimize biological variability due to differences in age and weight among rats.

In addition to the biomechanical parameters determined through torsional testing, the mode of failure can also provide substantial information. The mode of torsional failure as determined by gross inspection provided an indication as to the extent of healing. A spiral failure in the mid-diaphyseal region indicated a complete union while a transverse failure through the fracture site indicated a nonunion. A combination spiral/transverse failure indicated a partial union (FIG. 2).

Data and Statistical Analysis

Analysis of variance (ANOVA) was performed followed by Holm-Sidak post-hoc tests to determine differences (SigmaStat 3.0, SPSS Inc., Chicago, Ill.). A P value less than 0.05 was considered statistically significant.

Micro-CT Methods

Both fractured and non-fractured femora were dissected from each animal, wrapped in saline soaked gauze, and frozen in conical tubes at –20° C. following sacrifice. Femora were slowly defrosted in warm water and stored in an ice bath for transport after the intermedullary pins were carefully removed from the fractured femora. Fractured femora were scanned to determine bone mineral density (BMD), and polar moment of inertia for several hundred transverse evenly dispersed sections using a Skyscan 1172 micro-CT device (Kontich, Belgium). Acquired images were then reconstructed using Skyscan software. Following CT scans, femur dimensions and gauge lengths were measured using a digital caliper and torsionally tested as described above. Software developed by Morgan, E. F., et al. (*Bone.*, Oct. 25, 2008) was utilized to calculate the average effective polar moment of inertia of fractured femora via the transverse sections for each femur.

Figure 3:
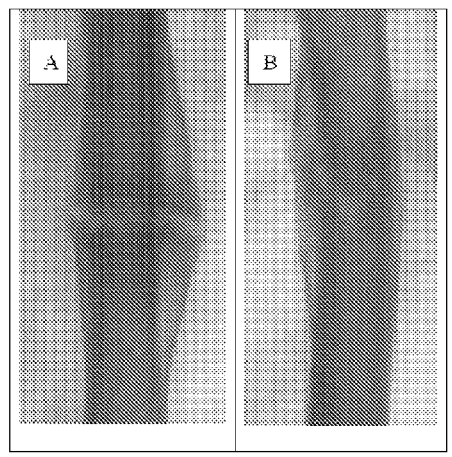
FIG. 3 contains four-week micro-CT images of surface modified rods: (A) boron coated control rod group; (B) 0.6 mg/Kg vanadium-boron coated rod group.

Non-weighted micro-CT shear values were calculated based on the inner and outer boundaries of the callus. These values do not take into account the tissue mineralization, but provide a precise measurement of callus polar moment of inertia. Weighted micro-CT shear values were determined based on the intensity of tissue in the scan. The resolution of the scan was set to 17.5 µm. Threshold values were set between 0.25 and 0.28, based on a protocol by Morgan et al., with a global threshold of approximately 25% of the maximum gray value of the scan. This corresponds to approximately 45% of the attenuation of mature cortical bone in the cohorts of specimens measured by Morgan et al. The threshold was used to distinguish mineralized tissue from poorly mineralized and unmineralized tissue. Lower polar moments of inertia, calculated based on higher intensities (larger percentage of mineralized tissue), result in higher shear values. Micro-CT scans were also analyzed to determine commonly investigated CT parameters. At 4 and 5 weeks post-fracture resected femora were evaluated in terms of bone mineral density (BMD), bone volume fraction (BVF or BV/TV), and trabecular mineralized tissue thickness (Tb. Th.). The results are shown in FIG. 3 and Table 5.

Vanadium Atomic Absorption Spectrophotometry

BB Wistar rats were anesthetized and confirmed to be non-responsive to external stimuli before beginning the surgical procedure. The anesthetized rats were exsanguinated by cardiac puncture using a 10 ml syringe with a 22 gauge needle after shallow puncture just lateral to the sternum and through the intercostal space. Following puncturing the dermis and cardiac wall, slight backpressure was placed on the plunger to withdraw blood from the ventricle. The collected blood was transferred to an appropriate container used for collection of plasma (heparinized) or serum (non-heparinized). Following the cardiac puncture, the rats were euthanized via cervical dislocation. The pin was removed from the intermedullary canal of the fractured femora and stored in a clean conical tube. Other rod samples pre-implantation were also stored in conical tubes and appropriately labeled prior to atomic absorption spectrophotometry analysis.

Each preparation involved drying 100 ml and 50 ml beakers to a constant weight before introducing samples. Accompanying each batch of samples, were NIST 1643d water, which has a certified value for vanadium concentration and method blanks. After the 100 ml beakers and contents were brought to constant weight, the rods were dissolved in Aqua Regia. The solution was quantitatively transferred to a centrifuge tube and spun. The supernatant was then transferred to a 50 ml volumetric flask. This process was repeated three times with the addition of distilled water (DW) to each tube as a rinse. After the final rinse and transfer to the 50 ml flask, each flask was diluted to the volume mark. Rod residue from the centrifuge tube was quantitatively transferred to a constant weight 50 ml beaker with multiple DW washes. After the last wash, beakers were placed on a hotplate with a surface temperature of 125 degree Celsius. The beaker contents were evaporated and then placed in a 105 degree Celsius oven and brought to constant weight. Sulfuric acid was added to the beaker and heated. The dissolved contents were transferred to a 25 ml volumetric flask. Solutions were analyzed after appropriate dilution by Zeeman Heated Graphite Atomization Atomic Absorption Spectrophotometry. Data from spectrometer output were transferred to appropriate computer software for further analysis and sample vanadium level quantification. All excess mineral acid was discarded according to EOHSS procedures for hazardous materials disposal. All glassware was washed and prepared before analysis and after.

Results

General Health

In this biomechanical experiment, animals among treatment groups were age matched. There was no statistical difference among treatment groups in percent weight gain from the time of surgery indicating that vanadium injected locally into the intramedullary canal had no effect on metabolism (Table 2). Blood glucose levels and age at surgery showed a significant difference between the Vanadium-Boron coated and saline groups (Table 2); however, the clinical relevance of this observation is difficult to ascertain since this range is within the normoglycemic value of Non-DM rats. These fluctuations may be a result of the small sample size and variations based on diet.

All animals were grouped within the same age within 40 days (80-120 days) and the difference between the average ages between these two groups was less than 10 days. Such a small age difference within this phase is unlikely to produce any major changes in healing rates.

TABLE 2

General Health of Non-DM BB Wistar Rats: Local Vanadium (VAC) Delivery without a Carrier (Mechanical Testing)

|  | Blood Glucose (mg/dl)* Pre-Surgery | Age at Surgery | % Weight gain |
|---|---|---|---|
| Saline (n = 5) | 81.7 ± 4.3 | 99.0 ± 1.0 | 3.5 ± 2.3 |
| Boron Coated (n = 3) | 91.0 ± 4.1 | 89.0 ± 0.0 | 15.3 ± 8.14 |
| Vanadium-Boron Coated (n = 4) | 90.6 ± 2.1 | 89.0 ± 0.0 | 14.5 ± 1.3 |

The data represents average values±standard deviation

Microradiographic Evaluation

Using a five-point radiographic scoring system, 0=partial callus formation, 1=definite callus with bony union on one cortex, 2=definite callus with bony union on two cortices, 3=definite callus with bony union on two cortices, and 4=definite callus with bony union on all four cortices, at 4 weeks post-fracture femurs treated with the vanadium-boron coated rod demonstrated significantly higher scores than control femurs (Table 3).

TABLE 3

Radiographic Scoring Evaluation†

|  | 4 Weeks Post-Fracture (# of cortices bridged) | |
|---|---|---|
|  | Cortical Healing | Endosteal Healing |
| Saline Control | 0.67 ± 0.29 (n = 3) | 1.33 ± 0.29 (n = 3) |
| Vanadium-Boron Coated | 4.0 ± 0.0* (n = 5) | 2.4 ± 0.0 (n = 5) |

†The data represents average values ± standard deviation
*Represent values statistically higher than control, $p < 0.05$ Mechanical Testing Results The effect of local vanadium therapy on healing of femur fractures in normal (non-diabetic) rats was measured by torsional mechanical testing. At 4 weeks post-fracture, rats treated with vanadium displayed improved mechanical properties of the fractured femora compared to the untreated group. The maximum torque to failure, (Saline group vs. Vanadium-Boron rod group P<0.05), and maximum torsional rigidity (Saline group vs. Vanadium-Boron rod group P<0.05), were both significantly increased compared in the Vanadium-Boron rod group when compared to the untreated group (Table 4). When the mechanical parameters of the fractured femora were normalized to the intact, contralateral femora, percent peak torque (Saline group vs. Boron rod group P<0.05, Saline group vs. Vanadium-Boron rod group P<0.05), torsional rigidity (Saline group vs. Vanadium-Boron rod group P<0.05), shear modulus (Saline group vs. Vanadium-Boron rod group P<0.05), and shear stress (Saline group vs. Vanadium-Boron rod group P<0.05) were all significantly greater in the local vanadium treated groups when compared to the saline group (Table 4).

Our study demonstrated that local VAC bound to IM rods significantly improved the biomechanical parameters of fracture healing in non-diabetic animals. An earlier study examining the effect of vanadium on mechanical strength of bone in non-diabetic and diabetic animals revealed that vanadium had no effect on bone homeostasis in non-diabetic animals (Facchini D M, et al., *Bone,* 2006; 38(3):368-377). The fracture healing pathway is different than the bone homeostasis pathway. This is likely the primary reason for conflicting results presented in both models. Other possibilities include different dosages and delivery methods in each study.

TABLE 4

Four weeks Post-fracture mechanical testing with vanadium (VAC)[†]

| | Fractured femur values | | | |
|---|---|---|---|---|
| | Maximum Torque to failure (Nmm) | Maximum Torsional Rigidity (Nmm$^2$/rad) | Shear Modulus (MPa) | Maximum Shear Stress (MPa) |
| Saline (n = 5) | 178 ± 38 | 9,363 ± 5,032 | 235 ± 102 | 19 ± 3 |
| Vanadium-Boron Coated (n = 4) | 305 ± 30* | 31,078 ± 6,917* | 2,347 ± 1,649 | 60 ± 33 |

| | Fractured femur values normalized to the contralateral (intact) femur | | | |
|---|---|---|---|---|
| | Percent maximum torque to failure | Percent maximum torsional rigidity | Percent shear modulus | Percent maximum shear stress |
| Saline (n = 5) | 30 ± 18 | 19 ± 11 | 4 ± 2 | 11 ± 5 |
| Vanadium-Boron Coated (n = 4) | 76 ± 9* | 107 ± 36* | 38 ± 19* | 40 ± 20* |

[†]The data represents average values ± standard deviation
*Represents values significantly greater than the saline control group; $p < 0.05$

Micro-CT Results

Micro-CT analysis of fractured and contralateral femora at 4 weeks post-fracture did not reveal any significant differences in effective polar moment of inertia, bone mineral density, or trabecular thickness between the VAC-boron coated group and boron coated control group (Table 5). Bone volume fraction however, was significantly higher (p<0.05) for VAC-boron coated group than boron coated control group at 4 weeks post-fracture (Table 5) Micro-CT images at 4 weeks post-fracture suggest accelerated healing for the VAC-boron coated group, compared to the boron coated control group (FIG. 3).

TABLE 5

Four weeks Post-fractureMicro-CT Analysis with Surface Modified Vanadium-Borided Rods

| | Effective Polar Moment of Inertia (mm$^4$) | Micro-CT Modified Effective Polar Moment of Inertia (mm$^4$) | Micro-CT Modified Effective Polar Moment of Inertia Weighted (mm$^4$) |
|---|---|---|---|
| Boron Coated Control Rod (n = 5) | 69 ± 30 | 49 ± 7 | 22 ± 4 |
| 0.6 mg/Kg Vanadium-Boron Coated Rod (n = 5) | 49 ± 24 | 48 ± 10 | 23 ± 5 |

| | Volumetric Bone Mineral Density (g/cm$^3$) | Volumetric Bone Mineral Density normalized to Intact Femora (%) | Bone Volume Fraction (BV/TV %) | Trabecular Thickness (µm) |
|---|---|---|---|---|
| Boron Coated Control Rod (n = 5) | 0.86 ± 0.03 | 51 ± 2 | 88.0 ± 1.8 | 71 ± 11 |
| 0.6 mg/Kg Vanadium-Boron Coated Rod (n = 5) | 0.84 ± 0.04 | 50 ± 2 | 90.4 ± 1.1* | 79 ± 8 |

The data represents average values ± standard deviation
*Represents values statistically higher than boron coated control group; $p < 0.05$ versus boron coated control.

Vanadium Quantification Results in Stainless Steel Implants

Figure 4:
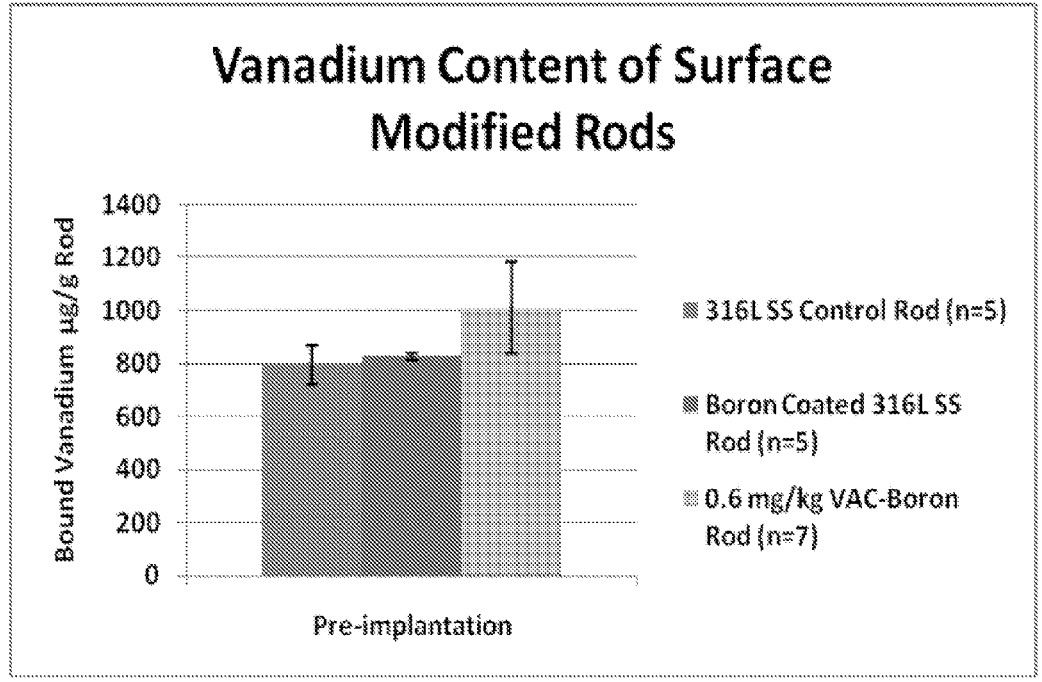
FIG. 4 illustrates results of the vanadium content of the surface-modified rods from analysis of locally-bound vanadium pre-implantation within surgical Kirschner wire.
Figure 5:
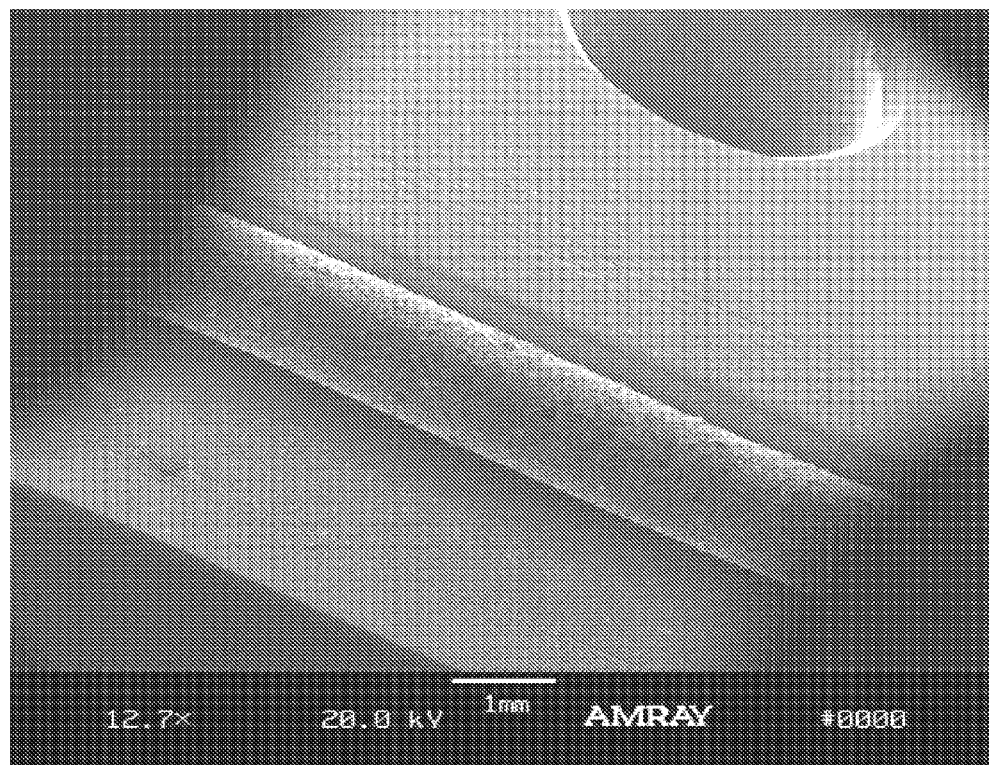
FIG. 5 contains a scanning electron microscope (SEM) image of Ti6Al4V implant as visualized under SEM at 12.7× (scale 1 mm).

When the vanadium content of surgical rods prior to implantation and 4 weeks post-fracture was quantified, levels of vanadium in VAC-boron coated rods were significantly higher (p<0.05) than those of boron coated control rods, prior to implantation and at 4 weeks post-fracture (Table 6). Additionally, levels of vanadium averaged amongst all runs of rod production, calculated pre-implantation, were similar for untreated rods compared to boron control rods (FIG. 4).

Vanadium levels in pack borided implants were calculated by adding the mass of vanadium that was dissolved in aqua regia, and the remaining "residue" dissolved in sulfuric acid, normalized to total implant mass. Table 6 summarizes normalized vanadium content in each component of the coated rods. Bound vanadium per gram rod weight in both the aqua regia dissolved portion of the implant and the remaining residue dissolved in sulfuric acid were significantly higher (p<0.05) in VAC-boron coated rods than boron coated control rods, prior to implantation and at 4 weeks post-fracture (Table 6). VAC-boron coated rods and boron control rods had significant decreases in bound vanadium per gram weight within the residue at 4 weeks post-fracture, compared to pre-implantation values (Table 6).

TABLE 6

Analysis of Locally Bound Vanadium Pre- and Post-implantation within Surgical K-wire

| | Total Bound Vanadium per gram rod weight (μg) | Bound Vanadium per gram rod weight (μg) after dissolving rod in aqua regia | Bound Vanadium per gram rod weight (μg) in residue after dissolving rod in sulfuric acid |
|---|---|---|---|
| Pre-implantation | | | |
| Boron Coated Control Rod (n = 5) | 831 ± 21 | 800 ± 0 | 1,783 ± 179 |
| 0.6 mg/Kg Vanadium-Boron Coated Rod (n = 5) | 1,186 ± 129* | 1,142 ± 112* | 2,408 ± 9*,# |
| 4 Weeks Post-Fracture | | | |
| Boron Coated Control Rod (n = 5) | 805 ± 27 | 831 ± 21 | 1,414 ± 108 |
| 0.6 mg/Kg Vanadium-Boron Coated Rod (n = 5) | 1,084 ± 54* | 1,052 ± 56* | 1,334 ± 56 |

The data represents average values ± standard deviation
*Represents values statistically higher than boron coated control group; $p < 0.05$ versus boron coated control.

SEM and EDX Results of Ti6Al4V Implants

Vanadium levels in VAC surface coated Ti6AL4V implants showed that both rod samples contained a greater percentage of vanadium than is found in this alloy (FIGS. 6 and 7). These results suggest that vanadium coated to these implants.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims. All references cited hereby are incorporated by reference in their entirety.

What is claimed is:

1. An implantable orthopedic device coated by a composite surface coating, said coating comprising an insulin-mimetic vanadium compound.

2. The implantable orthopedic device of claim 1, wherein the insulin-mimetic vanadium compound comprises an organovanadium compound having a structure of formula $VOL_2$ or $VO(OR)L_2$, wherein L is a bidentate monoprotic ligand, and R is an organic group.

3. The implantable orthopedic device of claim 2, wherein L is a bidentate monoprotic ligand selected from hydroxamates, 2,4-diones, α-hydroxypyrones, α-hydroxypyridi-nones, and amino acids; and R is selected from $C_1$-$C_6$ alkyl, phenyl, benzyl or $C_2$-$C_6$ alkenyl group, each optionally substituted by one to three substituents independently selected from hydroxyl, $C_1$-$C_4$ alkyl, and halogen.

4. The implantable orthopedic device of claim 1, wherein said insulin-mimetic vanadium compound is selected from the group consisting of vanadyl acetyl-acetonate (VAC), vanadyl sulfate (VS), vanadyl 3-ethylacetylacetonate (VET), bis(malto-lato)oxovanadium (BMOV), bis(kojato)oxovanadium(IV), bis(3-oxy-1,2-dimethyl-4-pyridinonato)-oxovanadium(IV), bis(2-hydroxymethyl-5-oxy-1-methyl-4-pyridinonato)-oxovanadium(IV), bis[2-(2'-oxy-phenyl)-2-oxazolinato]-oxovanadium(IV), bis[2-(2'-oxyphenyl)-2-thiazolinato]-oxovana-dium(IV), bis(benzohydroxamato)-oxovanadium(IV), bis(benzohydroxamato)-methoxo-oxovanadium(V), bis(benzohydroxamato)-ethoxooxo-vanadium(V), bis(salicylaldehyde)-oxovanadium(IV), ammonium bis(maltolato)-dioxo-vanadate, bis(ethylmalto-lato)oxovan-adium(IV), oxovanadium(IV) biguanide, oxovanadium(IV) metformin, oxovanadium(IV) phenformin, and vanadyl cysteine complexes.

5. The implantable orthopedic device of claim 1, wherein said insulin-mimetic vanadium compound is selected from the group consisting of vanadyl acetylacetonate (VAC), vanadyl sulfate (VS), vanadyl 3-ethylacetylacetonate (VET), and bis(maltolato)oxovanadium (BMOV).

6. The implantable orthopedic device of claim 1 selected from the group consisting of plates, rods, screws, implants and arthroplasty implants.

7. The implantable orthopedic device of claim 1, wherein the underlying device is made of stainless steel.

8. The implantable orthopedic device of claim 7, wherein the stainless steel is 316L.

9. The implantable orthopedic device of claim 1, wherein the underlying device is made of a titanium alloy or cobalt-chrome.

10. The implantable orthopedic device of claim 9, wherein the titanium alloy is Ti6AL4V.

11. An insulin-mimetic agent composite surface coating for an implantable orthopedic device, comprising an insulin-mimetic organovanadium compound.

12. The insulin-mimetic agent composite surface coating of claim 11, wherein the organovanadium compound has a structure of formula $VOL_2$ or $VO(OR)L_2$, wherein L is a bidentate monoprotic ligand, and R is an organic group.

13. The insulin-mimetic agent composite surface coating of claim 12, wherein L is a bidentate monoprotic ligand selected from hydroxamates, 2,4-diones, α-hydroxy-pyrones, α-hydroxypyridinones, and amino acids; and R is selected from $C_1$-$C_6$ alkyl, phenyl, benzyl or $C_2$-$C_6$ alkenyl group, each optionally substituted by one to three substituents independently selected from hydroxyl, $C_1$-$C_4$ alkyl, and halogen.

14. The insulin-mimetic agent composite surface coating of claim 13, wherein the organovanadium compound is selected from the group consisting of vanadyl acetyl-acetonate (VAC), vanadyl sulfate (VS), vanadyl 3-ethylacetylacetonate (VET), bis(malto-lato)oxovanadium (BMOV), bis(kojato)oxovanadium(IV), bis(3-oxy-1,2-dimethyl-4-pyridinonato)-oxovanadium(IV), bis(2-hydroxymethyl-5-oxy-1-methyl-4-pyridinonato)-oxovanadium(IV), bis[2-(2'-oxyphenyl)-2-oxazolinato]-oxovanadium(IV), bis[2-(2'-oxy-phenyl)-2-thiazolinato]-oxovanadium(IV), bis(benzohydroxamato)-oxovanadium(IV), bis(benzohydroxamato)-methooxovanadium(V), bis(benzohydroxamato)-ethoxooxo-vanadium(V), bis(salicylaldehyde)-oxovanadium(IV), ammonium bis(maltolato)-dioxo-vanadate, bis(ethylmaltolato)oxovanadium(IV), oxovanadium(IV) biguanide, oxovanadium(IV) metformin, oxovanadium(IV) phenformin and vanadyl cysteine complexes.

15. The insulin-mimetic agent composite surface coating of claim 11, wherein said insulin-mimetic agent is selected from the group consisting of vanadyl acetylaceton-ate (VAC), vanadyl sulfate (VS), vanadyl 3-ethylacetylacetonate (VET) and bis(malto-lato)oxovanadium (BMOV).

16. A method of promoting bone healing in a patient in need thereof comprising treating the patient with an implantable orthopedic device coated by a composite surface coating according to claim 11.

17. The method of claim 16, wherein composite surface coating comprises vanadyl acetylacetonate (VAC).

18. The method of claim 16, wherein the implantable orthopedic device is selected from the group consisting of plates, rods, screws, implants, arthroplasty implants, and orthopedic devices.

19. The method of claim 16, wherein the implantable orthopedic device is a bone implant.

20. The method of claim 16, wherein said patient is afflicted with a bone condition selected from the group consisting of bone fracture, bone trauma, arthrodesis, and bone deficit conditions associated with post-traumatic bone surgery, post-prosthetic joint surgery, post-plastic bone surgery, post-dental surgery, bone chemotherapy treatment, congenital bone loss, post traumatic bone loss, post surgical bone loss, post infectious bone loss, allograft incorporation or bone radiotherapy treatment.

21. The method of claim 16, wherein the method is used in conjunction with administration of a cytotoxic agent, cytokine or growth inhibitory agent.

22. The method of claim 16, wherein the method is used in conjunction with administration of a bioactive bone agent.

23. The method of claim 16, wherein the method is used for treatment of fractures, osseous defects, delayed union or nonunion, allograft/autograft incorporation or tendon/ligament osseous junction.

24. The method of claim 23, wherein the method is used in conjunction with an allograft/autograft or orthopedic biocomposite.

25. The method of claim 16, wherein said patient is a mammalian animal.

26. The method of claim 16, wherein said patient is a human.

27. The method of claim 16, wherein said patient is a non-diabetic human.

28. A method of promoting bone healing in a patient in need thereof comprising treating the patient with an implantable orthopedic device according to claim 1.

29. A method of making an implantable orthopedic device, comprising coating an implantable device with an insulin-mimetic agent composite coating according to claim 11.

30. The method of claim 29, wherein the insulin-mimetic agent composite coating comprises vanadyl acetylacetonate (VAC).

* * * * *

UNITED STATES PATENT AND TRADEMARK OFFICE
CERTIFICATE OF CORRECTION

| | | |
|---|---|---|
| PATENT NO. | : 9,144,633 B2 | Page 1 of 1 |
| APPLICATION NO. | : 13/992927 | |
| DATED | : September 29, 2015 | |
| INVENTOR(S) | : Sheldon S. Lin et al. | |

It is certified that error appears in the above-identified patent and that said Letters Patent is hereby corrected as shown below:

In the Related U.S. Application Data:

Page 1, at column 1, add "Provisional Application No. 61/454,061, filed March 18, 2011".

Signed and Sealed this
Thirty-first Day of May, 2016

Michelle K. Lee
*Director of the United States Patent and Trademark Office*